United States Patent
Rezac et al.

(10) Patent No.: US 7,583,378 B2
(45) Date of Patent: Sep. 1, 2009

(54) SPECTROGRAPH CALIBRATION USING KNOWN LIGHT SOURCE AND RAMAN SCATTERING

(75) Inventors: Jeromy P. Rezac, Albuquerque, NM (US); Thomas H. Chyba, Tijeras, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 381 days.

(21) Appl. No.: 11/418,107

(22) Filed: May 5, 2006

(65) Prior Publication Data

US 2009/0015829 A1 Jan. 15, 2009

Related U.S. Application Data

(60) Provisional application No. 60/775,797, filed on Feb. 23, 2006.

(51) Int. Cl.
*G01J 3/44* (2006.01)
*G01N 21/65* (2006.01)

(52) U.S. Cl. .................. 356/301; 356/326; 356/328

(58) Field of Classification Search .......... 356/301, 356/326, 328
See application file for complete search history.

(56) References Cited

U.S. PATENT DOCUMENTS

| | | | | |
|---|---|---|---|---|
| 5,303,165 A * | 4/1994 | Ganz et al. | .................. | 356/319 |
| 5,452,084 A | 9/1995 | Mitchell et al. | | |
| 5,553,616 A * | 9/1996 | Ham et al. | .................. | 600/316 |
| 5,652,653 A * | 7/1997 | Alsmeyer et al. | ............ | 356/301 |
| 5,850,623 A * | 12/1998 | Carman et al. | ................ | 702/28 |
| 5,933,792 A * | 8/1999 | Andersen et al. | .............. | 702/32 |
| 5,986,756 A * | 11/1999 | Slater et al. | ................. | 356/301 |
| 6,072,577 A * | 6/2000 | Wunderling et al. | ........ | 356/301 |
| 6,141,095 A * | 10/2000 | Allen et al. | .................. | 356/301 |
| 6,351,306 B1 * | 2/2002 | Tedesco et al. | .............. | 356/301 |
| 6,608,677 B1 * | 8/2003 | Ray et al. | ..................... | 356/301 |
| 6,675,106 B1 * | 1/2004 | Keenan et al. | ................ | 702/28 |
| 6,734,420 B2 * | 5/2004 | Empedocles et al. | ........ | 250/271 |
| 7,158,225 B2 * | 1/2007 | Tedesco et al. | .............. | 356/301 |
| 7,388,202 B2 * | 6/2008 | Sterling et al. | ......... | 250/339.07 |
| 2007/0263213 A1 * | 11/2007 | Stedman | ..................... | 356/328 |

OTHER PUBLICATIONS

ASTM E-1683-02, "Standard Practice for Testing the Performance of Scanning Raman Spectrometers", ASTM International, West Conshohocken, PA, United States, 2002.

ASTM E-1840-96 (Reapproved 2002), "Standard Guide for Raman Shift Standards for Spectrometer Calibration", ASTM International, West Conshohocken, PA, United States, 2002.

(Continued)

*Primary Examiner*—Kara E Geisel
(74) *Attorney, Agent, or Firm*—Edell, Shapiro & Finnan, LLC (57) ABSTRACT

A method is provided for calibrating a spectrometer device used for Raman scattering analysis. A predetermined dispersion curve for a diffraction grating or spectrograph of the spectrometer device is modified based on spectrum data associated with detected dispersed light from a calibration light source to produce a modified dispersion curve. The wavelength of a Raman light source on a light detection device is determined. Calibration data for the spectrometer device is computed from the Raman line peak positions for the first chemical, the wavelength on the detection device of the Raman light source and the modified dispersion curve.

24 Claims, 8 Drawing Sheets

OTHER PUBLICATIONS

Gregory W. Faris et al., "Ratio of Oxygen and Nitrogen Raman Cross Sections in the Ultraviolet", vol. 36, No. 12, Optical Society of America, 1997.

PCT International Search Report and Written Opinion in counterpart International Application No. PCT/US07/62665, dated Feb. 20, 2008.

* cited by examiner

SPECTROGRAPH CALIBRATION USING KNOWN LIGHT SOURCE AND RAMAN SCATTERING

RELATED APPLICATION

This application claims priority to U.S. Provisional Application No. 60/775,797 filed Feb. 23, 2006, the entirety of which is incorporated herein by reference.

BACKGROUND OF THE INVENTION

The present invention relates to spectrometers, and more particularly to a technique for spectrograph calibration.

Spectrometer devices are useful in monitoring for the presence of certain types of chemicals. For example, a spectrometer device may use principles of Raman scattering to analyze a liquid, solid or gas material for certain chemicals. In one type of spectrometer device, a light dispersing element (also referred to as a spectrograph or diffraction grating) is provided to disperse light from a sample and the dispersed light is detected by a detector, such as a charge-coupled camera device. Pixels on the detector are activated depending on the nature of the dispersed light and data representing the spectrum produced by the detector is analyzed to determine the presence of one or more chemicals.

The performance of a spectrometer depends on the mechanical alignment of its components, on temperature and pressure conditions in and around the device, and in particular on the light dispersing element. To ensure accuracy of the measurements and analysis made by a spectrometer, it is necessary to adjust or calibrate for such variations.

SUMMARY OF THE INVENTION

Briefly, a method is provided for calibrating a spectrometer device used for Raman scattering analysis. A predetermined dispersion curve for a diffraction grating or spectrograph of the spectrometer device is modified based on spectrum data associated with detected dispersed light from a calibration light source to produce a modified dispersion curve. The wavelength of a Raman light source on a light detection device is determined. Calibration data for the spectrometer device is computed from the Raman line peak positions for the first chemical, the wavelength on the detection device of the Raman light source and the modified dispersion curve.

DETAILED DESCRIPTION

Figure 1:
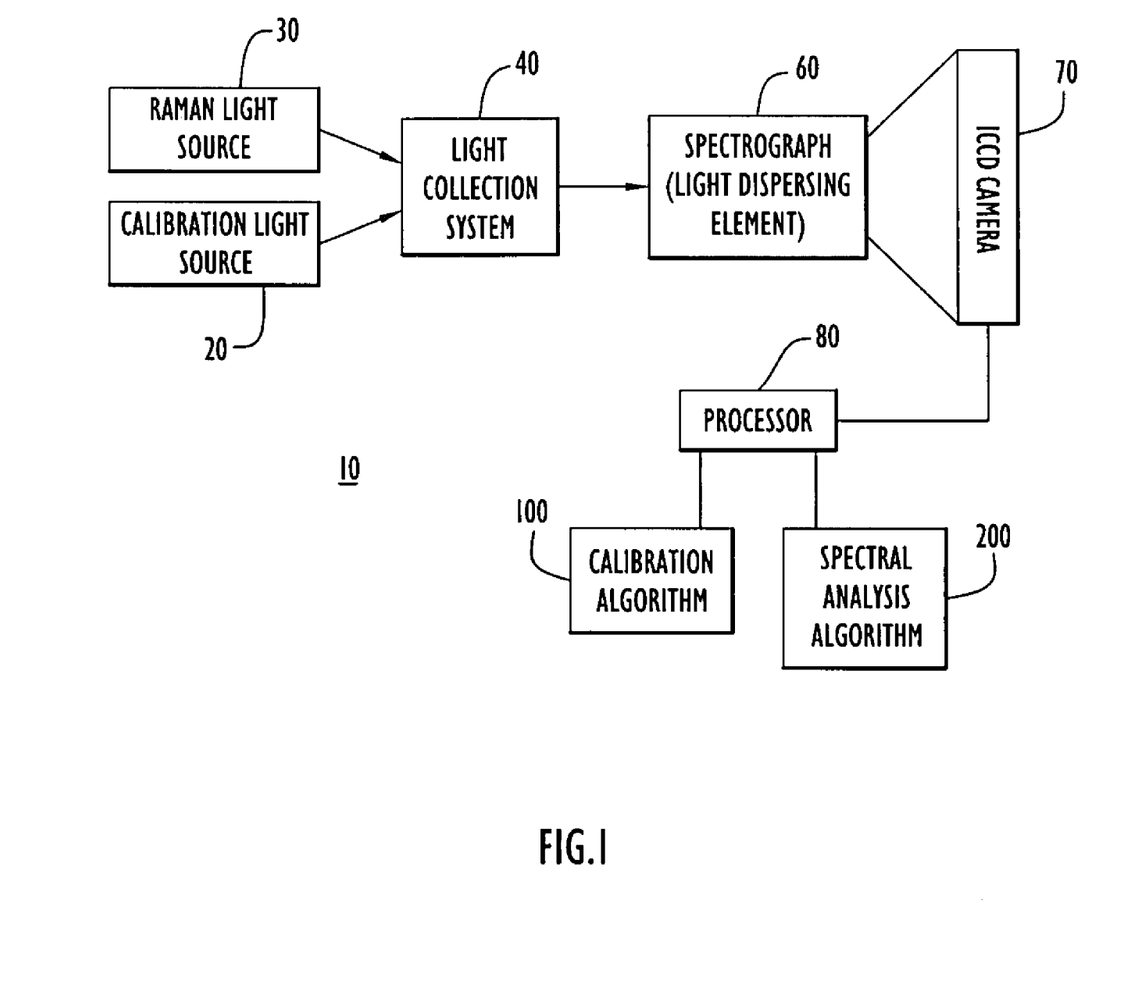
FIG. 1 is a block diagram of a spectrometer device having calibration capability according to an embodiment of the invention.

Referring first to FIG. 1, a spectrometer system or device according to an embodiment of the present invention is generally shown at reference numeral 10. The spectrometer system 10 comprises a calibration light source 20 and a Raman light source 30. A light collection system 40 collects light and is coupled to a spectrograph 60 which serves as the light dispersing element. In one embodiment, the light collection system 40 may comprise an auto-focused telescope and an optical fiber 50 that couples the light collected by the telescope to the spectrograph 60. An intensified charge-coupled device (ICCD) camera 70 is optically coupled to the spectrograph 60 and is in turn coupled to a signal processor (processor) 80. The processor 80 executes a calibration algorithm 100 (described hereinafter) and a spectral analysis algorithm 200, such as a Raman scattering algorithm. The processor 80 may be more generally referred to as a control unit since it may also perform other control functions of the spectrometer 10.

The desired Raman scattering effect is measured when the Raman light source 30 is activated and the spectrometer 10 is in a measurement mode. The Raman light source 30 can be any narrow band light source used for Raman excitation. In an exemplary embodiment, the light source 30 is an ultraviolet (UV) excimer laser. The calibration light source 20 may be any stable wavelength source and may include an undetermined number of spectral lines within the spectral region of interest. In an exemplary embodiment, the calibration light source 20 is a mercury (Hg) lamp. Alternatively, the calibration light source 20 may be an Argon (Ag) lamp or any fixed wavelength light source (laser) having a desired and known spectrum.

As is known in the art, a diffraction grating, such as the spectrograph 60, has a theoretical curve of dispersion vs. wavelength number expressed in terms of ICCD pixels and can be approximated as a polynomial curve, in an exemplary embodiment it is a cubic polynomial curve. The manufacturer of the grating typically provides data describing this curve. Thus, the dispersion curve function is previously determined either by measurement or theory. According to an embodiment of the present invention, the calibration algorithm 100 calibrates the dispersion curve of the spectrograph 60. This calibration algorithm 100 may be invoked at any time to verify proper operation of the spectrometer and may be used with a calibration source that is built into the spectrographic system 10 or with a calibration light source that is external to the system 10. Moreover, this technique can be used for in-field measurements or bench-top measurements (under controlled or test conditions).

On the ICCD camera 70, the pixels are a certain width across, but the wavelength to pixel mapping is non-linear as a result of the light dispersing function of the spectrograph 60 that spreads out the wavelengths at different angles. This is a basic aspect of a spectrograph. Because the light dispersing function is non-linear, it is necessary to have knowledge about how that dispersion works, through calibration. Calibration for the spectrograph 60 involves determining the mapping of wavelengths to pixel numbers on the ICCD camera 70. Part of calibration involves mapping out wavelength vs. pixel number, and then factoring in the Raman signature of interest fixed in wavenumber space. As is known in the art, wavenumber space is in units (1/cm) and is the difference in wavenumbers between the Raman light source 30 and the Raman shifted light. To do this, it is necessary to determine the Raman light source wavelength on the ICCD camera 70 because although the Raman wavenumber signatures are fixed with respect to the Raman light source, the Raman wavelength signatures are dependent on the Raman light source wavelength. Factors that can change the wavelength calibration include temperature, pressure and small mechanical changes in the alignment. The wavelength to wavenumber calibration can also be changed by a shift in the Raman light source wavelength.

Figure 2:
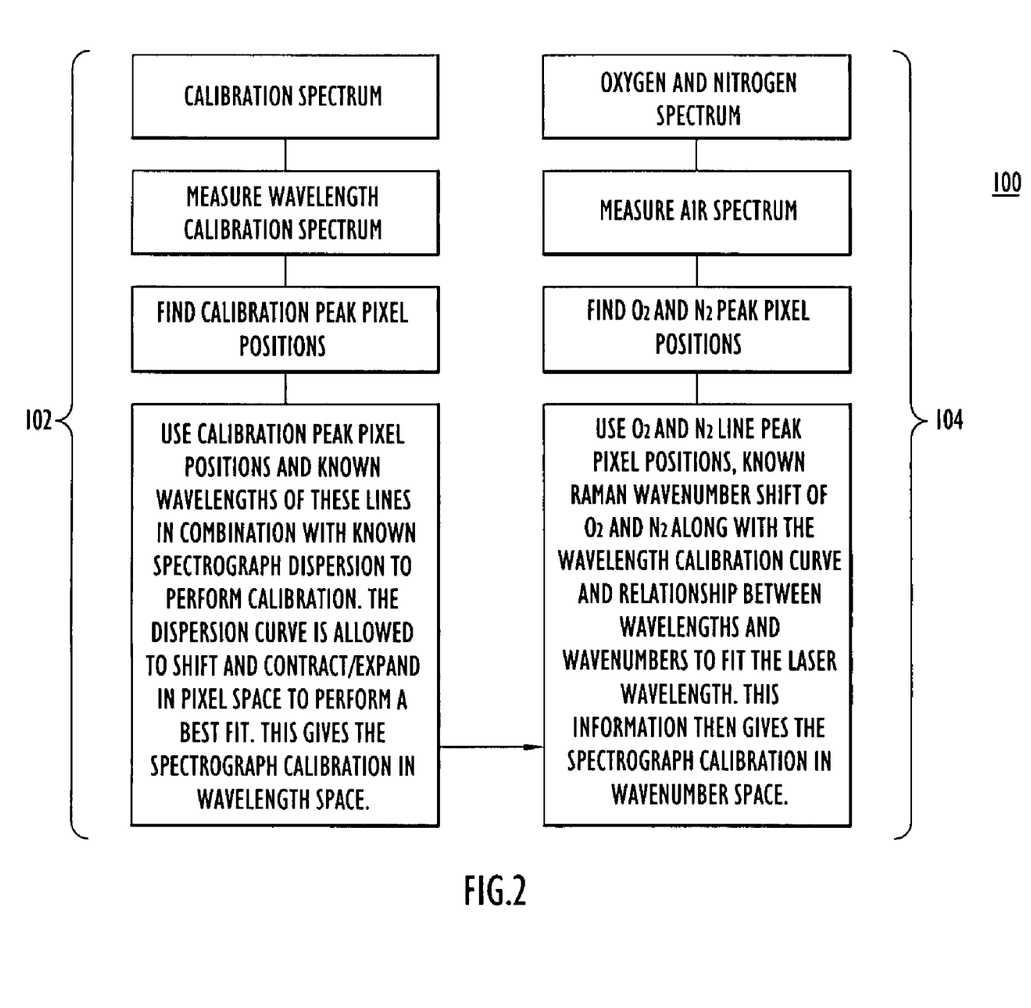
FIG. 2 is a generalized flow diagram depicting two basic computations performed during calibration according to an embodiment of the invention.

With reference to FIG. 2 in conjunction with FIG. 1, the calibration algorithm 100 is generally described. The calibration algorithm 100 may be viewed as a two stage process comprising obtaining the calibration spectrum at 102 and then obtaining the Raman air spectrum at 104. The starting point is the predetermined dispersion curve for the spectrograph. The (onboard or external) calibration light source 20 is activated and the resulting spectrum is obtained. The peak position of the calibration light source lines in the captured spectrum and known expected wavelengths of these lines are used to modify the dispersion curve for the spectrograph 60 to best fit the calibration light source lines. In particular, the dispersion curve is shifted along with contracting or expanding it, along the wavelength axis, which has the effect of changing the coefficients of the terms in the dispersion curve. The calibration light source line center positions are determined by fitting the spectral peaks near their peaks, and avoiding effects such as side mode structure at the bases of the peaks. The calibration light source 20 allows for a mapping of the spectrograph wavelengths to the ICCD pixels based on the dispersion curve and known line peak positions for the calibration light source 20.

Next, the spectrum is obtained for air by activating the Raman light source 30 and collecting the Raman scattered light associated with air. Peak pixel positions for first and second chemicals in the reference sample spectrum data are determined. In one embodiment, the first chemical is nitrogen ($N_2$) and the second chemical is oxygen ($O_2$) and their fractional peak pixel locations are determined by a fit to a Lorentzian lineshape function. Using the $O_2$ and $N_2$ peak pixel positions in the reference sample (e.g., air) spectrum data, known Raman wavenumber shift of $O_2$ and $N_2$, together with the modified dispersion curve and relationship between wavelengths and wavenumbers, the best fit for the Raman light source wavelength is determined. This in turn provides spectrographic calibration information in wavenumber space. It should be understand that while air is used as the reference sample when activating the Raman light source, the reference sample used may be a liquid, solid or gas. Air is only an example of a reference or calibration sample for the Raman light source that may be convenient for certain applications according to one embodiment.

The nitrogen and oxygen peak line positions and the modified dispersion curve allow one to determine the wavelength of the Raman light source 30 and to do a mapping in wavenumber space. The position of the nitrogen and oxygen lines on the ICCD's pixel array depend on the wavelength of the Raman light source, but the wavelength calibration light source peak line positions on the ICCD's pixel array do not depend on that wavelength. The line peak positions for calibration light source 20 provide a mapping of the wavelengths to the pixels. The nitrogen and oxygen peak position lines provide information about any shift in the Raman light source 30. The nitrogen and oxygen peak line positions are always the same number of wavenumbers away from that of the Raman light source 30.

Figure 3:
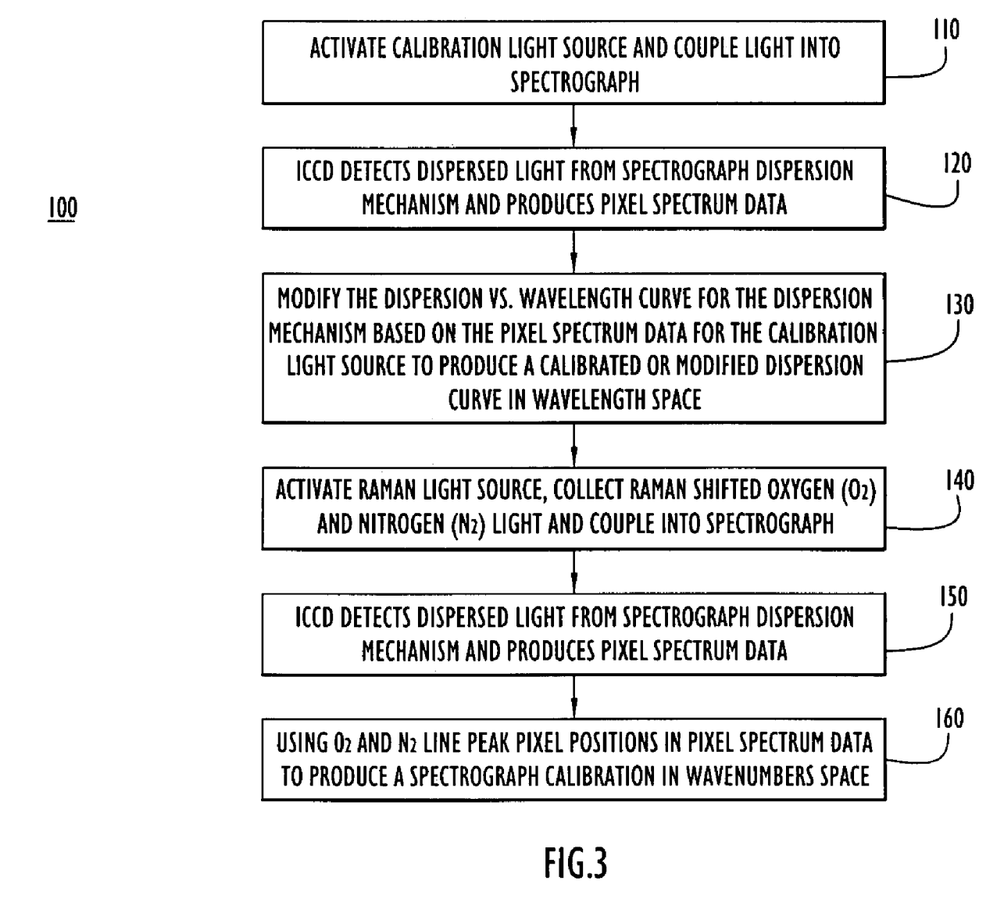
FIG. 3 is a flow chart depicting in more detail the calibration procedure according to an embodiment of the invention.
Figure 4:
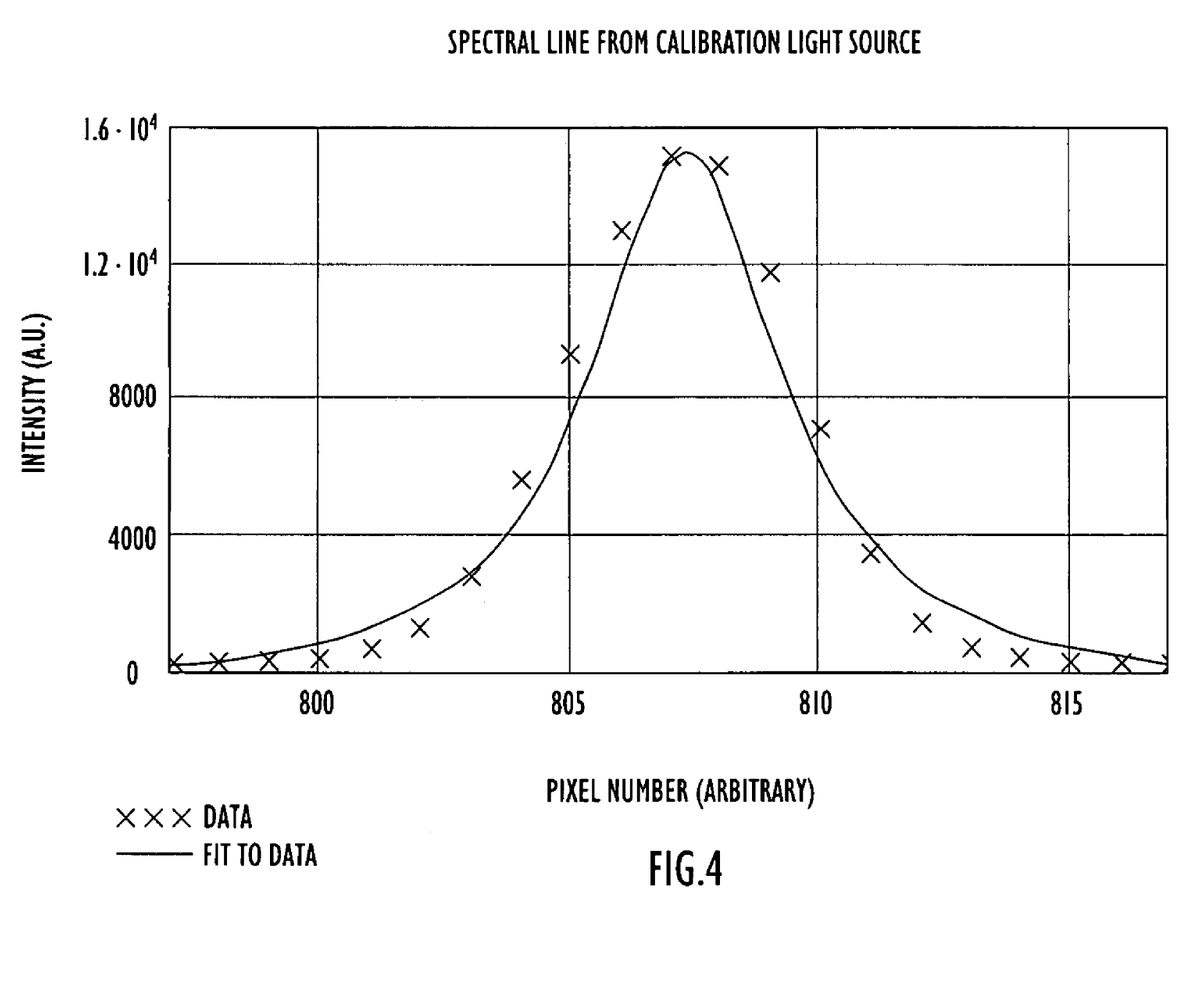
FIG. 4 is a plot showing an example of a spectral line produced from a calibration light source according to an embodiment of the invention.

Turning now to FIG. 3, in conjunction with FIGS. 1 and 4-8, the calibration algorithm 100 will be described in greater detail. At 110, the (onboard or external) calibration light source 20 is activated and the light is detected and coupled to the spectrograph 60 by the light collection system 40. At 120, the ICCD camera 70 detects the dispersed light from the spectrograph 60 and produces pixel spectrum data. FIG. 4 is a plot showing an example of a spectral line produced from a calibration light source according to an embodiment of the invention.

Figure 5:
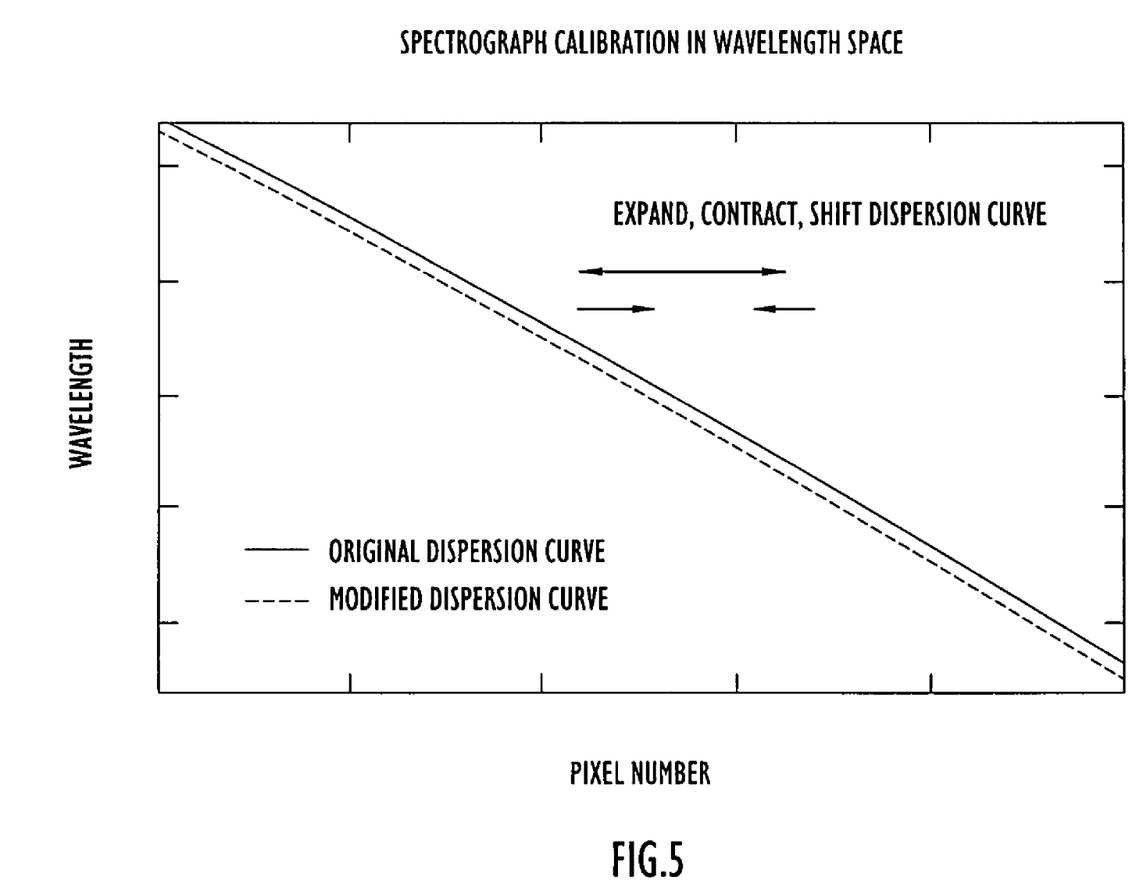
FIG. 5 is a diagram showing how the dispersion curve for the light dispersing element is modified based on the spectrum obtained by activation of the calibration light source according to an embodiment of the invention.

At 130, the processor 80 modifies the dispersion curve for the spectrograph 60 based on the pixel spectrum data for the calibration light source 20 to produce a calibrated or modified dispersion curve in wavelength space. Modification of the dispersion curve is shown in FIG. 5 according to one embodiment, where the dispersion curve from the spectrograph is shifted and expanded or contracted based on the spectrum data generated when the calibration light source 20 is activated.

Figure 6:
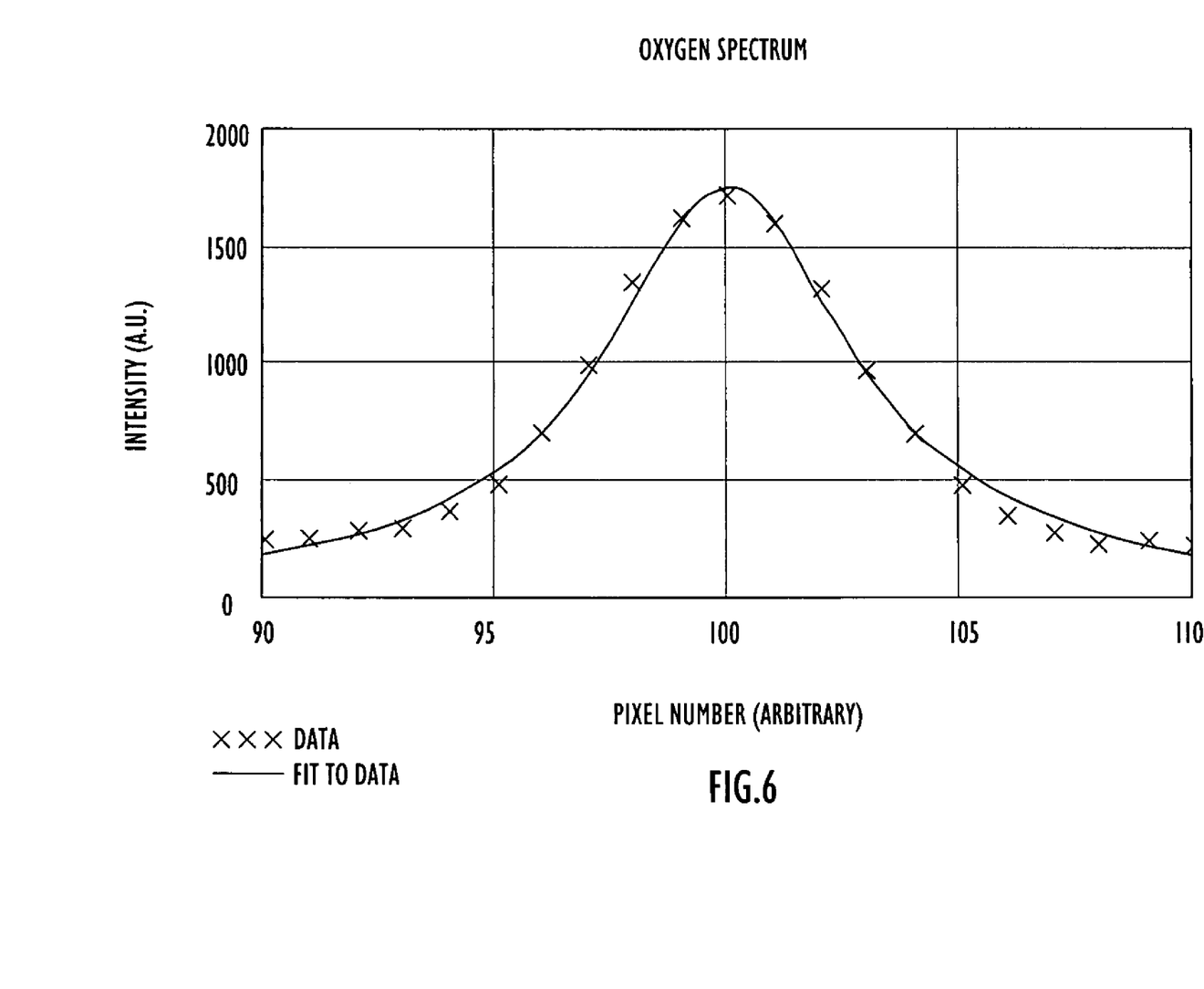
FIG. 6 is a plot showing an example of the peak spectral line for oxygen in a spectrum produced when the light source is activated and the light is dispersed onto the detector according to an embodiment of the invention.
Figure 7:
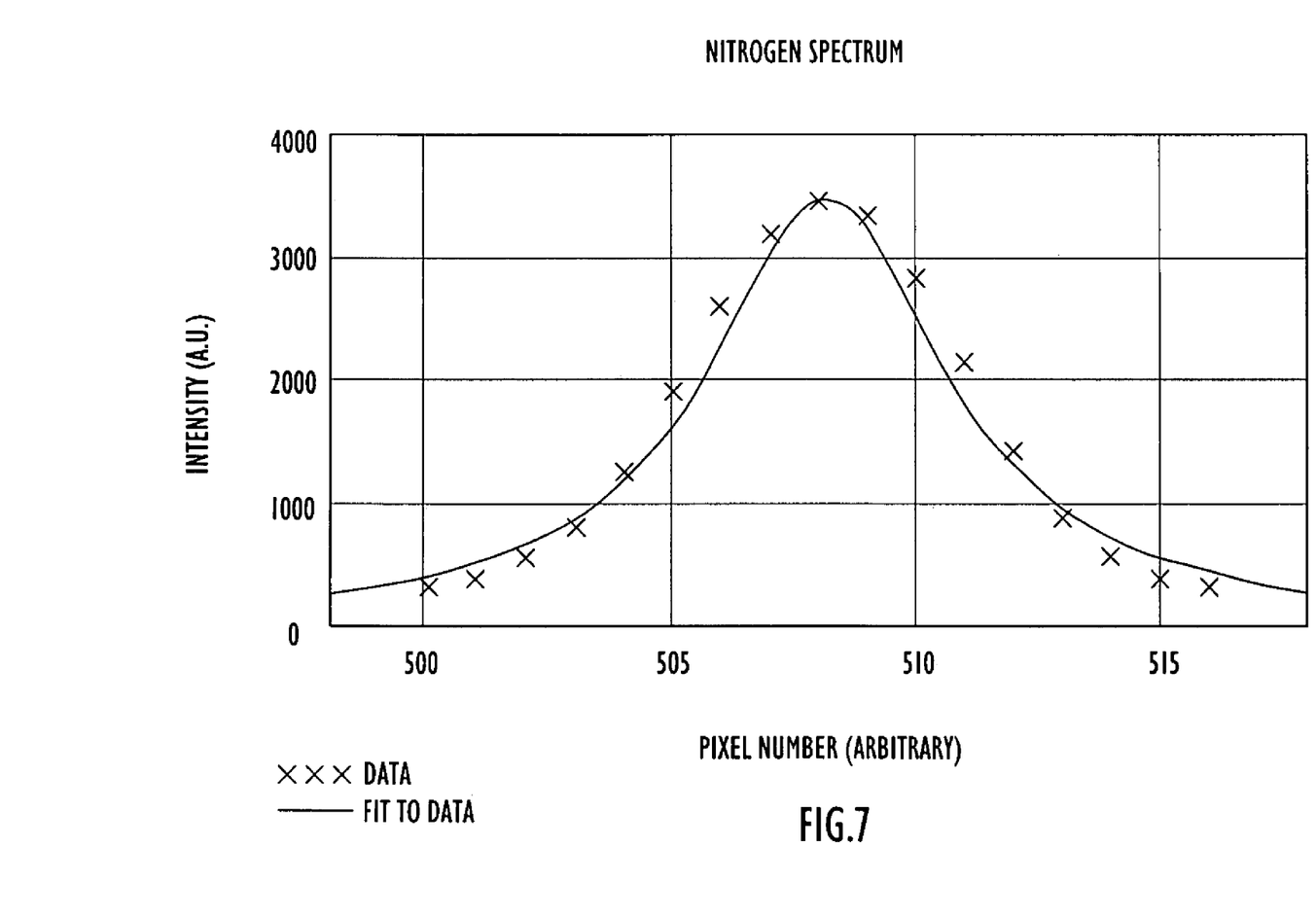
FIG. 7 is a plot showing an example of the peak spectral line for nitrogen in a spectrum produced when the light source is activated and the light is dispersed onto the detector according to an embodiment of the invention.

Next, at 140, the Raman light source 30 is activated into a reference sample, e.g., air, and the Raman shifted (scattered) light is collected and coupled to the spectrograph 60. At 150, the ICCD camera 70 detects dispersed light from the spectrograph 60 and produces spectrum data for the reference sample, e.g., air. FIG. 6 is a plot showing an example of the peak spectral line for oxygen derived from the air spectrum produced when the Raman light source is activated and the Raman scattered light is coupled into the spectrograph 60, dispersed, and detected with the ICCD camera 70 according to one embodiment. FIG. 7 is a plot showing an example of the peak spectral line for nitrogen in the air spectrum produced when the Raman light source 30 is activated and the Raman scattered light is coupled into the spectrograph 60, dispersed, and detected with an ICCD camera 70 according to one embodiment.

Figure 8:
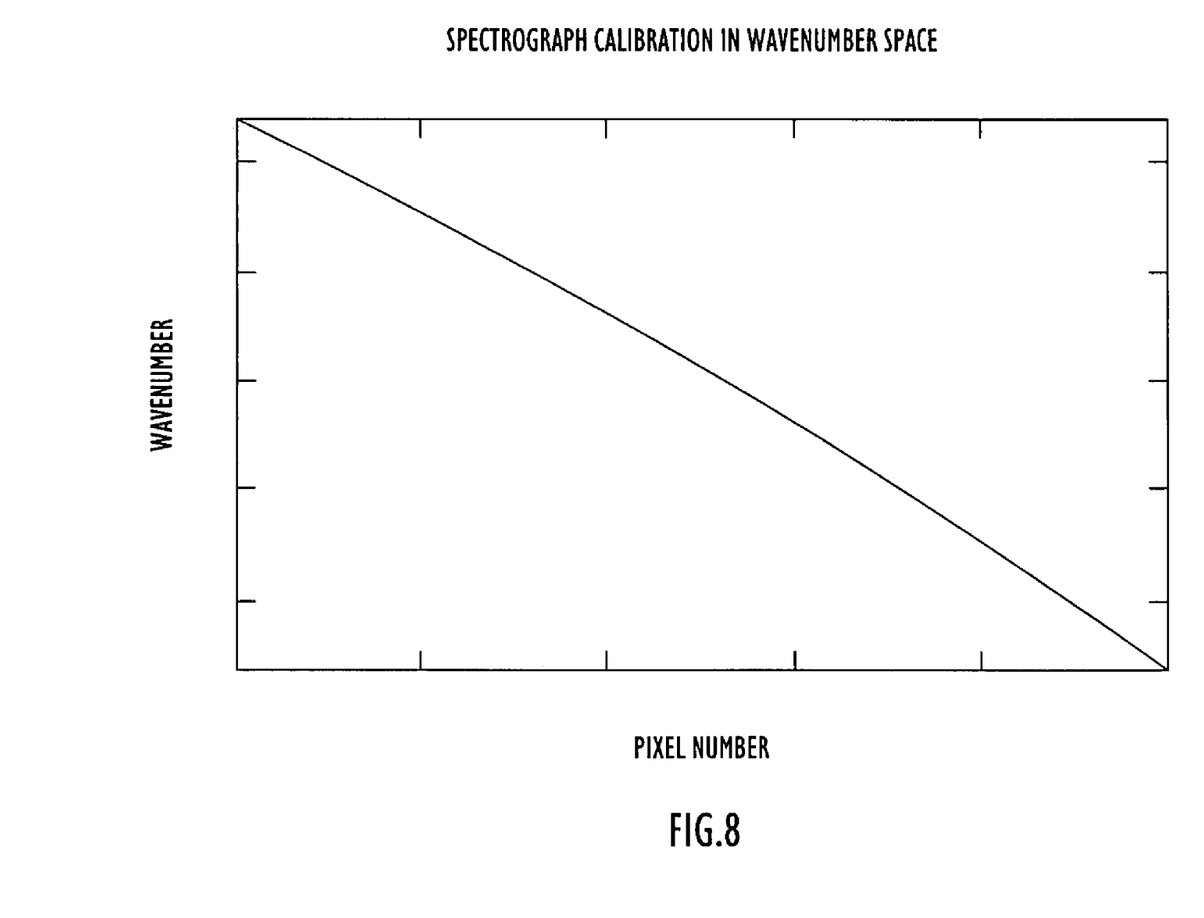
FIG. 8 is a plot showing calibration data in wavenumbers space produced from the modified dispersion curve and shifted spectral lines for nitrogen and oxygen according to an exemplary embodiment of the invention.

At 160, the oxygen and nitrogen line peak pixel positions in the air spectrum data are used, together with the known Raman wavenumber shift of oxygen and nitrogen and the modified dispersion curve, to best fit the Raman light source wavelength, and in so doing, produce spectrographic calibration information in wavenumber space. FIG. 8 is a plot showing exemplary calibration data in wavenumbers space produced from the modified dispersion curve and Raman shifted spectral lines for nitrogen and oxygen and the fitted Raman light source wavelength according to one embodiment. In this example, the Raman light source wavenumber value is zero.

The calibration technique described above may be used in the field to verify proper operation of the spectrometer. For example, during a test session, air spectrum data is obtained by activating the Raman light source into the air and collecting the Raman air spectrum. If the line peak positions for nitrogen and oxygen are acceptable, then it may not be necessary to activate the onboard calibration light source and execute the calibration algorithm 100. However, if the nitrogen and oxygen line peak positions are not acceptable, then the algorithm 100 is invoked using the onboard calibration light source and performing the curve fitting procedure using the measurements described above.

The calibration algorithm 100 in the embodiments described herein is very precise. However, it requires time to perform. Therefore, according to an embodiment of the invention, the spectrometer can monitor a real-time data stream (containing spectrum data) for the location of the nitrogen peak and automatically adjusts the calibration data (shift the data pixel number) so as to always keep the nitrogen peak in the data stream within a certain number of pixels (e.g., one pixel) of the position of the nitrogen spectral peak pixel number in the (previously computed) calibration data. This achieves fast recalibration albeit with less accuracy then the complete calibration algorithm 100. If the nitrogen peak drifts too far (greater than a predetermined threshold in pixels) from the calibration nitrogen peak pixel number over time, the processor may generate an alert (audible and/or visual) to the user so the user can initiate the more precise calibration algorithm 100. Thus, the spectrometer may constantly monitor the spectrum and initiate this "fast" calibration in real-time when appropriate and decide when the complete calibration algorithm 100 is needed and invoked.

In certain spectrometer applications many of the target chemicals and sample surfaces may have features that overlap the oxygen line, potentially confusing real-time monitoring. However, due to the physics of Raman spectra (i.e. the energy of chemical vibrational bonds), there are no (or extremely few) features interfering with the nitrogen line. Consequently, the nitrogen line is nearly always available with little interference from a surface being scanned or from chemicals on the surface. As a result, it is not necessary to change the mode of operation to locate the position of the nitrogen line.

The foregoing techniques are applicable to other types of spectrographic systems, such as those that operate in the infrared and UV, and in systems that use a narrowband light source other than a laser for creating the Raman scattering. Moreover, any spectral lamp with emission lines in the wavelength region of interest may be used as the calibration light source.

The system and methods described herein may be embodied in other specific forms without departing from the spirit or essential characteristics thereof. The foregoing embodiments are therefore to be considered in all respects illustrative and not meant to be limiting.

What is claimed is:

1. A method for calibrating a spectrometer device, comprising:
    a. activating a calibration light source to emit light that is coupled to a light dispersing element;
    b. detecting dispersed light from the light dispersing element to produce first spectrum data;
    c. modifying a dispersion curve for the light dispersing element based on said first spectrum data to produce a modified dispersion curve;
    d. detecting dispersed light produced as a result of activation of a light source that causes Raman scattering to produce second spectrum data;
    e. determining spectral line peak positions for a first chemical and for a second chemical in said second spectrum data; and
    f. computing calibration data for the spectrometer device from the spectral line peak positions for said first chemical, the spectral line peak positions for said second chemical, the known Raman wavenumber shifts for said first chemical and for said second chemical and said modified dispersion curve.

2. The method of claim 1, wherein (c) modifying comprises producing the modified dispersion curve in wavelength space.

3. The method of claim 1, wherein (c) modifying comprises shifting and expanding or contracting the dispersion curve for the light dispersing element to produce said modified dispersion curve based on peak pixel positions for the calibration light source.

4. The method of claim 3, wherein (f) computing comprises computing said calibration data in wavenumber space based further on a relationship between wavelengths and wavenumber, thereby fitting the modified dispersion curve to an operating wavelength of the light source that causes Raman scattering.

5. The method of claim 1, wherein (e) determining comprises determining spectral line peak positions for nitrogen as said first chemical and spectral line positions for oxygen as said second chemical.

6. The method of claim 1, wherein the first chemical is nitrogen and the second chemical is oxygen, and further comprising monitoring spectrum data when the spectrometer device is in normal use; and determining whether the line peak positions for nitrogen has drifted more than a predetermined number of pixels from calibrated peak positions for nitrogen determined from said monitoring performed over a period of time, and further comprising repeating (a) through (f) when the spectral line peak positions for nitrogen are more than said predetermined number of pixels from said calibrated peak positions for nitrogen.

7. The method of claim 6, and further comprising adjusting said calibration data so as to keep the spectral line peak positions of nitrogen in the second spectrum data within a predetermined number of pixels of the calibrated line peak positions for nitrogen.

8. The method of claim 1, wherein (a) activating comprises activating a calibration light source that is part of said spectrometer device.

9. The method of claim 1, wherein (e) comprising determining spectral line peak positions of nitrogen as said first chemical.

10. The method of claim 1, wherein (d) detecting comprises detecting Raman scattered light associated with a reference sample, and wherein said reference sample is a solid, liquid or gas.

11. The method of claim 10, wherein (d) detecting comprises detecting Raman scattered light associated with air.

12. A method for calibrating a spectrometer device used for Raman scattering analysis, comprising:
    a. modifying a dispersion curve for a light dispersing element of the spectrometer device based on first spectrum data associated with dispersed light detected by a detection device to produce a modified dispersion curve;
    b. determining line peak positions for a first chemical and a second chemical in second spectrum data associated with Raman scattered light detected by said detection device; and
    c. computing calibration data for the spectrometer device from the line peak positions for said first chemical and for said second chemical, known Raman wavenumber shifts for said first chemical and for second chemical and said modified dispersion curve.

13. The method of claim 12, wherein (a) modifying comprises shifting, expanding or contracting the dispersion curve for the light dispersing element to produce said modified dispersion curve based on peak pixel positions for a calibration light source that is used to create the first spectrum data from which the modified dispersion curve is produced.

14. The method of claim 12, wherein (c) computing comprises computing said calibration data in wavenumber space based further on a relationship between wavelengths and wavenumber, thereby fitting the modified dispersion curve to a wavelength of a light source that causes the Raman scattering light.

15. The method of claim 12, wherein (b) determining comprises determining spectral line peak positions for nitrogen as said first chemical and oxygen as said second chemical.

16. The method of claim 12, wherein the first chemical is nitrogen and the second chemical is oxygen, and further comprising monitoring spectrum data when the spectrometer device is in normal use; and determining whether the line peak positions for nitrogen has drifted more than a predetermined number of pixels from calibrated peak positions for nitrogen determined from monitoring over a period of time, and further comprising repeating (a) through (c) when the spectral line peak positions for nitrogen are more than said predetermined number of pixels from said calibrated peak positions for nitrogen.

17. The method of claim 16, and further comprising adjusting said calibration data so as to keep the spectral line peak positions of nitrogen in the second spectrum data within a predetermined number of pixels from said calibrated peak positions for nitrogen.

18. The method of claim 12, wherein (b) determining comprises detecting Raman scattered light associated with a reference sample, and wherein said reference sample is a solid, liquid or gas.

19. The method of claim 18, wherein detecting comprises detecting Raman scattered light associated with air.

20. A spectrometer device, comprising:
    a. a light dispersing element;
    b. a detector that detects light dispersed by said light dispersing element;
    c. a calibration light source;
    d. a light source suitable for causing Raman scattering; and
    e. a control unit coupled to said detector, wherein said control unit calibrates the spectrometer device by:
        i. modifying a dispersion curve for the light dispersing element based on first spectrum data associated with detected dispersed light from said calibration light source, thereby producing a modified dispersion curve;
        ii. determining spectral line peak positions for a first chemical and for a second chemical in second spectrum data produced by the detector as result of activation of said light source suitable for causing Raman scattering; and
        iii. computing calibration data for the spectrometer device from the line peak positions for said first chemical and for said second chemical, known Raman wavenumber shifts for said first chemical and said second chemical and said modified dispersion curve.

21. The spectrometer device of claim 20, wherein said control unit modifies said dispersion curve of the light dispersing element by shifting, expanding or contracting data representing the dispersion curve for the light dispersing element to produce said modified dispersion curve based on peak pixel positions for a calibration light source that is used to create the first spectrum data.

22. The spectrometer device of claim 21, wherein said control unit computes said calibration data in wavenumber space based further on a relationship between wavelengths and wavenumber thereby fitting the modified dispersion curve to a wavelength of the light source suitable for causing Raman scattering.

23. The spectrometer device of claim 20, wherein said control unit determines spectral line peak positions for nitrogen as said first chemical and spectral line peak positions for oxygen as said second chemical.

24. The spectrometer device of claim 20, wherein the first chemical is nitrogen and the second chemical is oxygen, and wherein the control unit monitors spectrum data when the spectrometer device is in use and determines whether the line peak positions for nitrogen has drifted more than a predetermined number of pixels from calibrated peak positions for nitrogen determined from monitoring spectrum data over a period of time, and further comprising repeating said (i) modifying, (ii) determining and (iii) computing when the spectral line peak positions for nitrogen are more than said predetermined number of pixels from said calibrated peak positions for nitrogen.

* * * * *

UNITED STATES PATENT AND TRADEMARK OFFICE
CERTIFICATE OF CORRECTION

PATENT NO.        : 7,583,378 B2
APPLICATION NO.   : 11/418107
DATED             : September 1, 2009
INVENTOR(S)       : Jeromy P. Rezac et al.

Page 1 of 1

It is certified that error appears in the above-identified patent and that said Letters Patent is hereby corrected as shown below:

Column 1, line 42, replace "Raman light source" with -- light source --;
       line 45, replace "the wavelength on the detection device of" with -- known wavenumber shifts for the first chemical --;
       line 46, delete "the Raman light source".

Signed and Sealed this

Seventeenth Day of November, 2009

David J. Kappos
*Director of the United States Patent and Trademark Office*